United States Patent [19]

Cook et al.

[11] E Re. 28,754

[45] Reissued Mar. 30, 1976

[54] BED EGRESS ALARM CIRCUIT

[75] Inventors: Kenneth J. Cook, Oak Park; Norman H. Horwitz, West Bloomfield, both of Mich.

[73] Assignee: William Beaumont Hospital, Royal Oak, Mich.

[22] Filed: May 16, 1975

[21] Appl. No.: 578,206

Related U.S. Patent Documents

Reissue of:

[64] Patent No.: 3,852,736
Issued: Dec. 3, 1974
Appl. No.: 337,955
Filed: Mar. 5, 1973

[52] U.S. Cl. ..... 340/279; 340/278; 307/279; 200/85 R; 128/2 S

[51] Int. Cl.[2] ..... G08B 21/00

[58] Field of Search ..... 340/279, 421, 278, 240; 307/252 R, 279, 304, 296; 128/2 S; 200/85 R

[56] References Cited

UNITED STATES PATENTS

| | | | |
|---|---|---|---|
| 3,302,685 | 2/1967 | Ono et al. | 340/228.1 |
| 3,638,642 | 2/1972 | Heflin | 340/279 X |
| 3,658,052 | 4/1972 | Alter | 340/279 X |
| 3,727,606 | 4/1973 | Sielaff | 128/2 S |

FOREIGN PATENTS OR APPLICATIONS

| | | | |
|---|---|---|---|
| 1,145,514 | 3/1969 | United Kingdom | |
| 1,563,013 | 4/1970 | Germany | 307/251 |

*Primary Examiner*—John W. Caldwell
*Assistant Examiner*—William M. Wannisky
*Attorney, Agent, or Firm*—Cullen, Settle, Sloman & Cantor

[57] ABSTRACT

A condition responsive circuit for generating an output signal upon the opening of a switch. An FET draws nominal current when the switch is closed. When the switch is opened the FET conducts to generate an output. The output may include an audio alarm, an oscillator and a transmitter to generate an alarm at a distant location, or a visual indicator.

10 Claims, 4 Drawing Figures

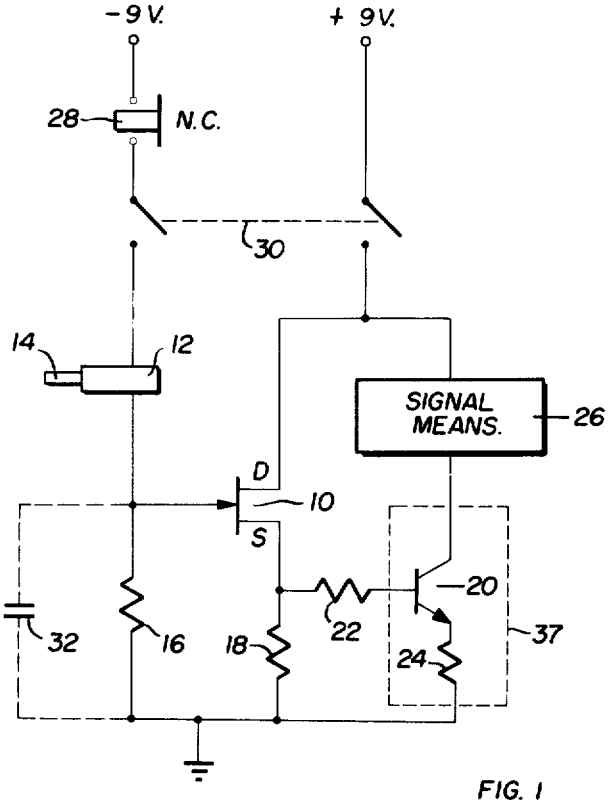
FIG. 1
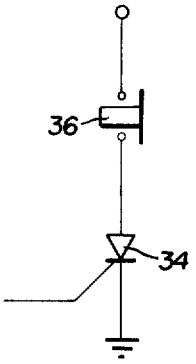
FIG. 2
FIG. 3
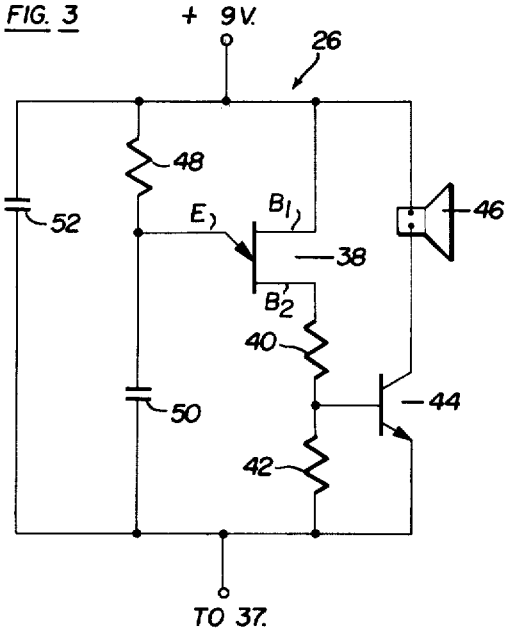
FIG. 4
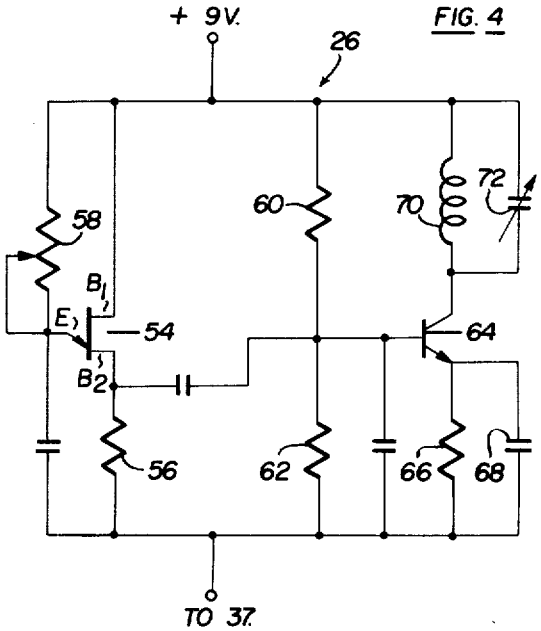

BED EGRESS ALARM CIRCUIT

Matter enclosed in heavy brackets [ ] appears in the original patent but forms no part of this reissue specification; matter printed in italics indicates the additions made by reissue.

BACKGROUND OF THE INVENTION

This invention relates generally to condition responsive circuits and, more particularly, to a condition responsive circuit which may be utilized in environments such as hospitals and the like for signalling the departure of a patient from a hospital bed.

One of the common hospital accidents occurs when a patient climbs off a hospital bed and injures himself such as by falling or stumbling. This will frequently occur when a patient who is too weak to walk unaided deliberately attempts to climb off the bed. It may also occur when the patient is not totally aware of his physical acts for one reason or another.

The departure of a patient from a hospital bed results in the removal of pressure (weight) from the bed. Therefore, the present invention is responsive to a change in conditions, namely, changes in pressure.

While various systems have been developed for detecting the presence or absence of pressure, it must be appreciated that in a hospital environment it is undesirable to have a hospital bed connected to a source of electric power. Not only is there a psychological problem when the bed itself is connected to a source of power, but there is always a danger of shock if liquids are spilled on the bed.

Therefore, if any current is to be supplied to the bed it must be nominal. However, if a self-contained battery system is utilized, the useful life of this system is quite short if the battery is always in an on condition.

It is therefore a principal object of the present invention to provide a condition responsive circuit which normally draws only a nominal current.

It is a further object of the present invention to provide a hospital bed alarm system which signals the departure of a patient from a bed.

It is yet another object of the present invention to provide a self-contained signal circuit responsive to a change in a physical condition, such as the presence or absence of pressure.

BRIEF DESCRIPTION OF THE DRAWINGS

The foregoing objects of the present invention together with other objects and advantages which may be attained by its use, will become more apparent upon reading the following detailed description, taken in conjunction with the drawings.

In the drawings, where like numeral identify corresponding parts:

FIG. 1 is a schematic circuit diagram of one embodiment of a condition responsive circuit;

FIG. 2 is a partial schematic illustration of a second embodiment of the present invention;

FIG. 3 is a schematic illustration of an alarm signalling circuit which may be utilized with the condition responsive circuit of the present invention; and FIG. 4 is a schematic diagram of a circuit for remote transmission of an alarm signal.

DETAILED DESCRIPTION OF THE INVENTION

Referring first to FIG. 1, there is shown a field effect transistor or FET 10 having source, drain and gate electrodes. A normally closed switch 12 having a plunger 14 is connected to the gate electrode of the FET 10. The junction of the switch 12 and the gate electrode are coupled through a resistance 16 to ground and the source electrode is coupled through a resistance 18 to ground.

A transistor 20 has its base electrode connected through a resistor 22 to the source electrode of the FET 10. The emitter of the transistor 20 is coupled through a resistor 24 to ground. Signal means 25 is coupled between the collector of transistor 20 and the drain electrode of the FET 10.

A source of voltage, such as −9 volts available from a small dry cell, is connected to one side of a normally closed switch 28. The other side of switch 28 is coupled to one pole of a double pole single throw switch 30 which serves as an on/off switch. The other side of the on/off switch is connected to switch 12.

The other pole of switch 30 connects a source of +9 volts, also from a dry cell, to the drain electrode of FET 10. Two separate dry cells are preferred for reasons to be explained.

OPERATION

In the use of the circuit of FIG. 1 in the environment of a hospital bed, it is important that only a nominal current be present to avoid a drain on the two batteries. Since it is desired to determined when a patient departs from the bed, the switch 12 having a plunger 14 may be a switch such as that manufactured by Packard Electric of Ohio, bearing Part No. 82A5A-1216876 which is a pressure sensitive switch. Thus, the pressure or weight on the switch is equivalent functionally to pressing and releasing on the plunger 14 shown schematically in FIG. 1.

With the on/off switch or double pole single throw switch 30 closed, there is a path from the −9 volt battery through the switch 12 to the gate of the FET 10 and through the resistor 16 to ground. Switch 12 is the type which is normally closed, that is, the plunger 14 is normally in. If the pressure sensitive switch is utilized, this represents the presence of a patient in a hospital bed. Under this condition, virtually no current flows through that portion of the circuit including the switch 12. The high voltage drop across resistor 16 which appears at the gate of the FET 10, biases the source to drain junction of the FET in an off condition.

Upon the departure of the patient from the bed, equivalent to the plunger 14 of the switch 12 being released, the circuit therethrough is opened removing the voltage source from the gate electrode of the FET 10. At this time, current will flow from the +9 volt source through one pole of the switch 30 and from the drain to the source electrode of the FET 10. This current flow turns on the transistor 20 permitting current to flow from the nine volt source through the signal means 26 to generate an output signal.

When the patient gets back into bed and his weight depresses the plunger 14 of the pressure sensitive switch, the signalling portion of the circuit is turned off.

An optional capacitor 32 coupled across resistor 16 provides a time delay. Thus, once the patient departs from the bed, the voltage at the gate of the FET 10 drops as the capacitor discharges. Once the capacitor has discharged, then the FET conducts to permit the alarm or signal to be given. The purpose of this optional capacitor 32, shown connected with dotted leads, is to prevent an immediate signalling if the patient momentarily moves clear of the switch while rolling over in bed.

The test or push button switch 28 is a normally closed switch which may be deliberately opened to test the operation of the system. Thus, opening the switch 28 is equivalent to opening the switch 12.

It must be appreciated that the portion of the circuit from the +9 volt battery across the FET and oscillator to ground normally draws no current. That is, no current flows to that portion of the circuit because the FET is biased off.

The current which flows through the portion of the circuit from the −9 volt battery and through the switch 12 is nominal because of the high resistance of resistor 16. However, since there is some nominal current, there is always the possibility that the −9 volt battery will lose power. However, the particular circuit of this invention has the additional feature that upon the loss of power of the −9 volt battery, the effect is the same as the opening of the switch 12. That is, the voltage at the gate of the FET 10 is removed and a signal is sounded.

As an alternate embodiment for the present invention, reference is made to FIG. 2 wherein there is illustrated a silicon controlled rectifier or SCR 34 having its cathode grounded and its anode connected to one side of a normally closed pushbutton switch 36. The embodiment of FIG. 2 replaces the portion of FIG. 1 shown in a dotted block 37 including the transistor 10 and the resistor 24. Thus, the gate of the SCR is connected to the resistor 22 and the side of the switch 36 not connected to the SCR is, of course, connected to the signal means 26.

The purpose of this embodiment is based upon the property of an SCR that once it fires or conducts it is necessary to actually remove the current from the anode to the cathode rather than taking away the signal from the gate. This provides the increased benefit of requiring a deliberate turn-off of the alarm by resetting switch 36.

With reference to FIG. 3, the first embodiment of an alarm is illustrated. This circuit may be utilized as the signal means 26 to generate an alarm at the hospital bed.

The audio alarm of FIG. 3 which is coupled between the drain electrode and the +9 volt source on one side and either the switch 36 of FIG. 2 or the transistor 20 of FIG. 1 on the other side includes an *UJT* [FET] 38 which is normally biased off and which has its [source] *base*$_2$ electrode connected to a voltage divider comprising two resistors 40 and 42. The junction of resistors 40 and 42 is coupled to the base of a transistor 44. The emitter of the transistor 44 is coupled back to the main circuit of FIGS. 1 or 2 and the collector of transistor 44 coupled to one side of a speaker 46. The other side of the speaker 46 is coupled back to the [drain] *base*$_1$ electrode of the *UJT* [FET] 38.

Also included in the alarm means of FIG. 3 is a resistor 48 [to provide a bias to the gate of the FET 38, a capacitor 50 coupling the gate of the FET back to the circuit of FIG. 1 or 2 and a] *and a capacitor 50 which form an RC timing network. The emitter of UJT 38 is connected to the common point between resistor 48 and capacitor 50. A* second capacitor 52 across the bias resistor 48 and the capacitor 50 *serves as a by-pass capacitor.*

In operation, when the patient leaves the bed thereby removing the bias from the FET 10, the conduction of the transistor 20 (or the SCR 34) as previously explained permits current to flow through the alarm or signal means of FIG. 3. This current flow [cuts off the bias to the FET 38 normally provided by the voltage drop across the resistor 48, and] *biases on the UJT 38. The voltage across the resistor 48 and capacitor 50 is time varying and when the UJT conducts, a current pulse is fed to* the voltage divider of resistors 40 and 42 *which* turns on transistor 44 to conduct the current through the speaker 46. The *UJT 38*, capacitor [s] *50* and resistor [s] *48* provide a [resonant] *time varying signal* circuit which provides the alarm to be driven through the speaker 46.

Since the alarm going off at the patient's bedside might startle the patients or otherwise create a disturbance, especially in the evening, another embodiment of the present invention contemplates the transmission of an alarm system to a remote area such as a nursing station. FIG. 4 discloses one such circuit which may be utilized as the signal means 26.

FIG. 4 includes a conventional unijunction oscillator to frequency modulate a radio frequency transmitter. The conventional unijunction oscillator includes an [FET] *UJT* 54 having its [source] *base*$_2$ electrode coupled through a resistor 56 back to the circuit of FIG. 1 or 2 and being [normally biased] in an off condition [by a voltage developed across a resistor 58 between the +9 volt source and the gate electrode.] When the transistor 20 of FIG. 1 or the SCR 34 of FIG. 2 conducts, current flows [through the resistor 58] and turns on the [FET] *UJT* 54. This functions as a [Colpits oscillator] *unijunction oscillator* to FM modulate a *Colpits oscillator* transmitter which includes a voltage divider network of resistors 60 and 62 having their junction coupled to the base of a transistor 64. The emitter of the transistor 64 is coupled by a parallel combination of a resistor 66 and a capacitor 68 back to the circuit of FIG. 1 and having the collector coupled to a parallel LC circuit comprising inductor 70 and variable capacitor 72. The transmitter of FIG. 4 operates in a conventional fashion.

Thus, there has been described a circuit for generating an output signal upon a change in condition, namely, a change in pressure. The output signal may generate an alarm at the location of the switch or by a radio frequency transmitter generating a signal at a remote station. The circuit is battery operated and draws essentially no current when the patient is in bed, thereby providing greater useful life for the batteries.

Various modifications may be made to the present invention. For example, the signal means may include a light or other signalling devices as are well known in the art. Furthermore, the pressure responsive switch 12 may be replaced by other condition responsive switches such as those which respond to the presence or absence of moisture. In that case, the circuit may be utilized to detect if a patient spills liquids in his bed or may be further utilized to detect the presence or absence of fluid flowing in a tube being utilized for intravenous feedings.

In the preferred embodiment of FIG. 1, FET 10 is a type 2N5653 and transistor 20 is a NPN–2N4400. Resistor 16 is 15M ohms, resistors 18 and 22 are 10K and 4.7K ohms, respectively, and capacitor 32 would be 0.22 uf for a two-second delay. In FIG. 2, the SCR 34 is a 2N5060.

The component values for the signal means of FIG. 3 are: [FET] *UJT* 38, 2N4871; transistor 44, 2N4400; resistors 40, 42 and 48, 470 ohms, 4700 ohms and 6.8K ohms, respectively, and capacitors 50 and 51 0.1 uf and 100 uf.

In FIG. 4, [FET] *UJT* 57–MU4894, transistor 64, 2N3294, resistors 56, 58, 60, 62 and 66; 47K, 500K, 33K, 10K and 1K, respectively, capacitor 68; 10pf and variable capacitor 72, 1.5–7p would provide suitable operation.

Therefore, the foregoing is a description of the preferred embodiment of circuitry only and should not be interpreted in a restrictive sense but only as exemplifying the underlying concepts of the present invention. The invention may be further developed within the scope of the following claims:

What is claimed is:

1. A condition responsive circuit for signalling the departure of a patient from a bed or the like by generating an output signal upon the opening of a switch, comprising:

a switch being normally closed by the weight of a patient in a bed;

an FET having source, drain and gate electrodes, said gate electrode connected to said switch for normally drawing only a nominal current and for continuously biasing said gate electrode to render said FET non-conductive;

a normally off output means coupled to said at least one of *said* source and drain electrodes for generating an output signal when said FET is rendered conductive;

the opening of said switch to remove the continuous bias from said gate electrode;

delay means coupled to said switch and said gate electrode for maintaining a bias at said gate electrode to prevent said FET from being rendered conductive for a predetermined time interval after the opening of said switch; and said output means including an SCR, an SCR switch, and a signal means, all connected in series;

said SCR being rendered conductive by said FET being rendered conductive to thereby generate an output signal from said signal means, and said SCR being thereafter rendered non-conductive only by operating said SCR switch.

2. A condition responsive circuit for signalling the departure of a patient from a bed or the like by generating an output signal upon the opening of a switch, comprising:

a switch being normally closed by the weight of a patient in a bed;

an FET having source, drain and gate electrodes, said gate electrode connected to said switch for normally drawing only a nominal current and for continuously biasing said gate electrode to render said FET non-conductive;

a normally off output means coupled to at least one of said source and drain electrodes for generating an output signal when said FET is rendered conductive;

the opening of said switch to remove the continuous bias from said gate electrode; and delay means coupled to said switch and said gate electrode for maintaining a bias at said gate electrode to prevent said FET from being rendered conductive for a predetermined time interval after the opening of said switch.

3. The circuit of claim [1] *2* and further including:

second switch means connected in series with said normally closed switch for testing the operation of said circuit by removing said continuous bias from the FET gate.

4. The circuit of claim [1] *2* wherein said output means includes a normally non-conductive electronic switch rendered conductive when said FET is rendered conductive.

5. The circuit of claim 4 wherein said output means further includes an oscillator coupled in series to said electronic switch, said oscillator being energized when said FET and said electronic switch are rendered conductive.

6. The circuit of claim 4 wherein said output means further includes a normally off transmitter which is turned on by said FET and said electronic switch being rendered conductive, the frequency of the transmitter being modulated by said oscillator.

7. The circuit of claim 4 wherein said electronic switch is an SCR.

8. The circuit of claim 7 and including third switch means in series with said SCR for rendering said SCR non-conductive after said SCR is rendered conductive by said FET being rendered conductive.

9. The circuit of claim [1] *2* wherein said switch is pressure sensitive.

10. The circuit of claim [1] *2* wherein said output means includes an audio alarm.

* * * * *